(12) United States Patent
Shiraishi (10) Patent No.: US 11,324,470 B2
(45) Date of Patent: May 10, 2022

(54) X-RAY DIAGNOSTIC APPARATUS, MEDICAL IMAGE PROCESSING APPARATUS, AND MEDICAL IMAGE PROCESSING METHOD

(71) Applicant: CANON MEDICAL SYSTEMS CORPORATION, Otawara (JP)

(72) Inventor: Kunio Shiraishi, Otawara (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 111 days.

(21) Appl. No.: 16/941,725

(22) Filed: Jul. 29, 2020

(65) Prior Publication Data

US 2021/0038180 A1 Feb. 11, 2021

(30) Foreign Application Priority Data

Aug. 6, 2019 (JP) .............................. JP2019-144631

(51) Int. Cl.
*A61B 6/00* (2006.01)
*G01T 1/02* (2006.01)
*G01T 1/161* (2006.01)

(52) U.S. Cl.
CPC .......... *A61B 6/5258* (2013.01); *A61B 6/5294* (2013.01); *A61B 6/542* (2013.01); *G01T 1/02* (2013.01); *G01T 1/161* (2013.01)

(58) Field of Classification Search
CPC ..... A61B 6/5258; A61B 6/5294; A61B 6/542; A61B 6/5205; A61B 6/06; G01T 1/02; G01T 1/161; G01T 1/17

USPC .......................................................... 378/62
See application file for complete search history.

(56) References Cited

U.S. PATENT DOCUMENTS

| 8,768,035 | B2* | 7/2014 | Liu | ........................ | A61B 6/585 |
| | | | | | 382/132 |
| 9,119,560 | B2* | 9/2015 | Kohara | .................. | A61B 6/461 |
| 2004/0234032 | A1 | 11/2004 | Nokita | | |
| 2013/0202085 | A1* | 8/2013 | Petrick | ..................... | H04N 5/32 |
| | | | | | 378/62 |
| 2016/0086548 | A1 | 3/2016 | Maeyama | | |

FOREIGN PATENT DOCUMENTS

| JP | 9-289985 A | 11/1997 |
| JP | 2003-185752 A | 7/2003 |
| JP | 2004-344249 A | 12/2004 |
| JP | 2009-153627 A | 7/2009 |
| WO | WO 2014/188813 A1 | 11/2014 |

* cited by examiner

*Primary Examiner* — David P Porta
*Assistant Examiner* — Gisselle Gutierrez
(74) *Attorney, Agent, or Firm* — Oblon, McClelland, Maier & Neustadt, L.L.P.

(57) ABSTRACT

An X-ray diagnostic apparatus according to an embodiment includes an X-ray tube, an X-ray detector, and processing circuitry. The X-ray tube exposes X-rays. The X-ray detector detects the X-rays exposed from the X-ray tube. The processing circuitry generates an X-ray image on the basis of a first detection result that is a detection result of the X-rays exposed for an irradiation period. The processing circuitry corrects the X-ray image on the basis of a second detection result that is a detection result of the X-rays until a point before the end of the irradiation period.

15 Claims, 8 Drawing Sheets

| EXPOSURE TIME | NUMBER OF DETECTION TIMES | PIXEL REGION | IRRADIATED X-RAY DOSE |
|---|---|---|---|
| yyyy/mm/dd hh:mm:ss | 1 | x1, y1 | ... |
| | | x2, y1 | ... |
| | | x2, y1 | ... |
| | | ⋮ | ⋮ |
| | | xn, yn | ... |
| yyyy/mm/dd hh:mm:ss | 2 | x1, y1 | ... |
| | | x2, y1 | ... |
| | | x2, y1 | ... |
| | | ⋮ | ⋮ |
| | | xn, yn | ... |
| ⋮ | ⋮ | ⋮ | ⋮ |
| yyyy/mm/dd hh:mm:ss | n-1 | x1, y1 | ... |
| | | x2, y1 | ... |
| | | x2, y1 | ... |
| | | ⋮ | ⋮ |
| | | xn, yn | ... |
| yyyy/mm/dd hh:mm:ss | n | x1, y1 | ... |
| | | x2, y1 | ... |
| | | x2, y1 | ... |
| | | ⋮ | ⋮ |
| | | xn, yn | ... |

X-RAY DIAGNOSTIC APPARATUS, MEDICAL IMAGE PROCESSING APPARATUS, AND MEDICAL IMAGE PROCESSING METHOD

CROSS-REFERENCE TO RELATED APPLICATIONS

This application is based upon and claims the benefit of priority from Japanese Patent Application No. 2019-144631, filed on Aug. 6, 2019; the entire contents of which are incorporated herein by reference.

FIELD

Embodiments described herein relate generally to an X-ray diagnostic apparatus, a medical image processing apparatus, and a medical image processing method.

BACKGROUND

Conventionally, an X-ray diagnostic apparatus configured to image an X-ray image by exposing, to a subject, X-rays from an X-ray tube and detecting, by a detector, the X-rays that have passed through the subject has been known. In the above-mentioned X-ray diagnostic apparatus, a phenomenon called "ghosting" occurs in some cases in which the sensitivity of detecting elements included in the detector is temporarily lowered with the X-rays incident on the detector and the contour of the subject imaged before appears in the X-ray image. In the above-mentioned X-ray diagnostic apparatus, a phenomenon "burn-in" also occurs in some cases in which the sensitivity of the detector becomes non-uniform due to deterioration in the detecting elements, or the like.

Conventionally, it can be difficult to correct the X-ray image with high accuracy when a phenomenon such as ghosting or burn-in occurs.

DETAILED DESCRIPTION

Hereinafter, embodiments of an X-ray diagnostic apparatus and a medical image processing apparatus will be described in detail with reference to the accompanying drawings.

First Embodiment

An X-ray diagnostic apparatus according to an embodiment includes an X-ray tube, an X-ray detector, and processing circuitry. The X-ray tube exposes X-rays. The X-ray detector detects the X-rays exposed from the X-ray tube. The processing circuitry generates an X-ray image on the basis of first detection results as detection results of the X-rays exposed for an irradiation period. The processing circuitry corrects the X-ray image on the basis of second detection results as detection results of the X-rays until a point before the end of the irradiation period.

Figure 1:
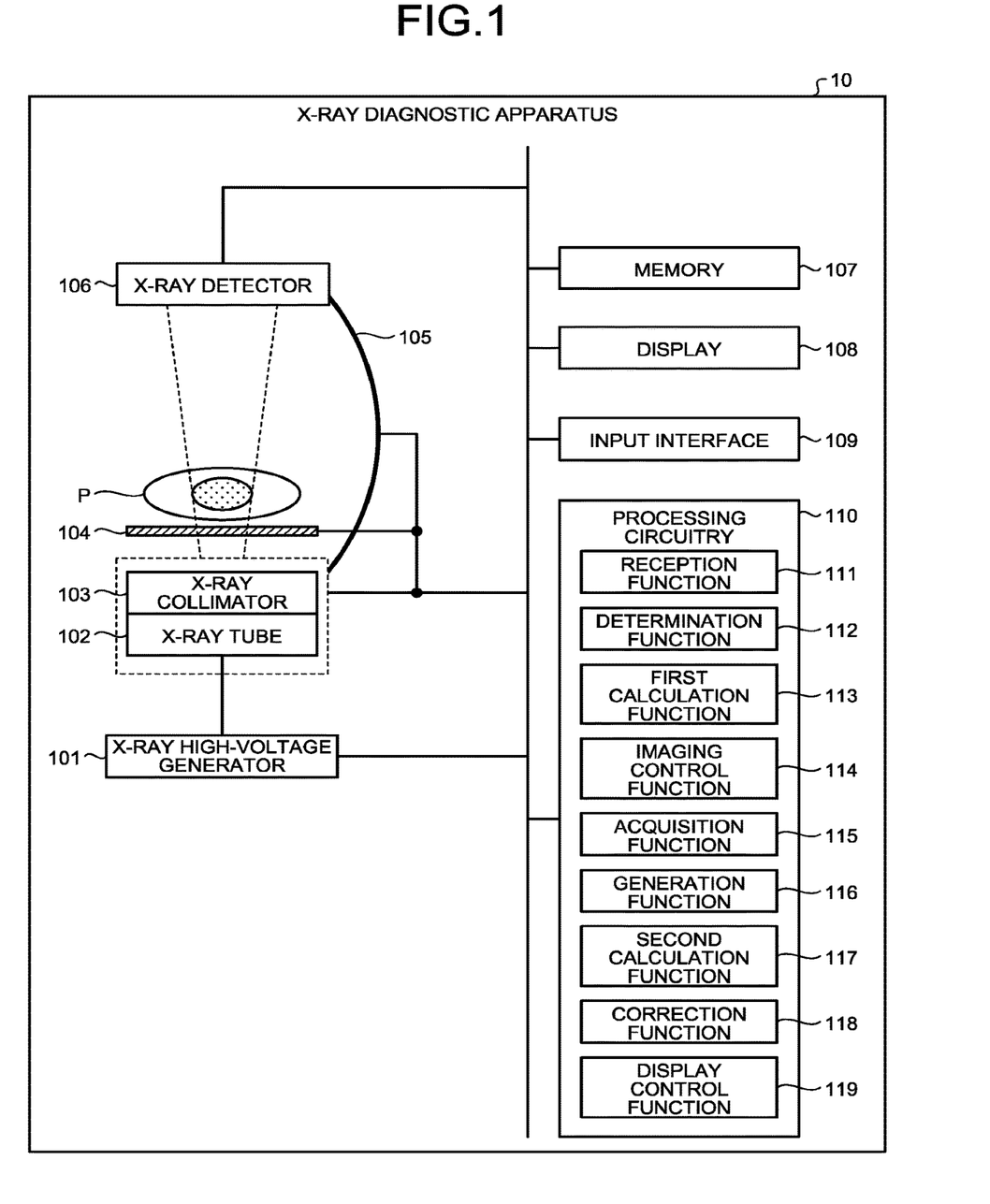
FIG. 1 is a diagram illustrating an example of the configuration of an X-ray diagnostic apparatus according to a first embodiment.

FIG. 1 is a diagram illustrating an example of the configuration of an X-ray diagnostic apparatus 10 in the embodiment. As illustrated in FIG. 1, the X-ray diagnostic apparatus 10 includes an X-ray high-voltage generator 101, an X-ray tube 102, an X-ray collimator 103, a tabletop 104, a C arm 105, an X-ray detector 106, memory 107, a display 108, an input interface 109, and processing circuitry 110. The X-ray diagnostic apparatus 10 in the embodiment is also referred to as a medical image processing apparatus. The X-ray diagnostic apparatus 10 can continuously image a plurality of X-ray images and is adaptable to moving images, for example, but is not limited thereto.

The X-ray high-voltage generator 101 supplies a high voltage to the X-ray tube 102 under control by the processing circuitry 110. The X-ray high-voltage generator 101, for example, has electric circuitry of a transformer, a rectifier, and the like, and includes a high-voltage generator configured to generate the high voltage to be applied to the X-ray tube 102 and an X-ray controller configured to control an output voltage in accordance with X-rays exposed from the X-ray tube 102. The high-voltage generator may be of a transformer system or of an inverter system.

The X-ray tube 102 is a vacuum tube having a cathode (filament) generating thermoelectrons and an anode (target) receiving collision of the thermoelectrons to generate X-rays. The X-ray tube 102 exposes the thermoelectrons to the anode from the cathode using the high voltage supplied from the X-ray high-voltage generator 101 to expose the X-rays. The X-ray tube 102 is also referred to as an X-ray exposer. In the embodiment, the X-ray tube 102 exposes the X-rays of a specified pulse width set by the processing circuitry 110 multiple times.

The X-ray collimator 103 has a collimator for narrowing an irradiation range of the X-rays exposed from the X-ray tube 102, a filter for adjusting the X-rays exposed from the X-ray tube 102, and a driving mechanism such as a motor and an actuator. The X-ray collimator 103, for example, operates the driving mechanism under control by the processing circuitry 110, which will be described later, to narrow the X-rays generated by the X-ray tube 102 so as to selectively irradiate a region of interest (ROI) of a subject P.

The tabletop 104 is a bed on which the subject P is placed and is arranged on a table device (not illustrated). The X-ray diagnostic apparatus 10 does not include the subject P.

The C arm 105 holds the X-ray tube 102, the X-ray collimator 103, and the X-ray detector 106 such that the X-ray tube 102 and the X-ray collimator 103 oppose the X-ray detector 106 with the subject P interposed therebetween. The C arm 105 has a driving mechanism such as a motor and an actuator and operates the driving mechanism under control by the processing circuitry 110, which will be described later, to be rotated and moved. Although in FIG. 1, the X-ray diagnostic apparatus 10 employs a single plane system, as an example, the embodiment is not limited thereto and a biplane system may be employed.

The X-ray detector 106 detects the X-rays from the X-ray tube 102 and outputs detection results to the processing circuitry 110. The X-ray detector 106 is also referred to as an X-ray detecting module.

The X-ray detector 106 is an X-ray flat panel detector (FPD) having a plurality of detecting elements aligned in a matrix form, for example. Each of the detecting elements of the X-ray detector 106 has a complementary metal oxide semiconductor (CMOS) sensor and a scintillator, for example. Each detecting element, for example, converts the detected X-rays into electric charges, accumulates them, and converts the accumulated electric charges into a voltage or a current to generate a detection signal. Each detecting element outputs the converted detection signal to the processing circuitry 110 as the detection result of the X-rays. Each detecting element corresponds to one pixel of an X-ray image based on the detection results.

A grid for reducing the dose of scattered rays incident on the detecting elements is provided on the surface of the X-ray detector 106. The grid has, for example, a pattern structure in which foils of aluminum or the like transmitting the X-rays and foils of lead or the like absorbing the X-rays are alternately arranged.

The scattered rays are X-rays, among the X-rays exposed from the X-ray tube 102, that have passed through the subject P and have been scattered by the subject P in passage. On the other hand, X-rays, among the X-rays exposed from the X-ray tube 102, that are linearly incident on the detecting elements from a focal point of the X-ray tube 102 are direct rays.

The X-ray detector 106 has an electric shutter function capable of acquiring detection results of the X-rays at desired acquisition timing under control by the processing circuitry 110. The X-ray detector 106, for example, reads, from the detecting elements, the detection results of the X-rays exposed till the acquisition timing and outputs them to the processing circuitry 110 during exposure of the X-rays by the X-ray tube 102, that is, in parallel with exposure of the X-rays by the X-ray tube 102. A well-known technique of the shutter function can be employed, and for example, an electronic shutter function of the CMOS sensors may be used.

The X-ray detector 106 has X-ray sensitivity setting of a plurality of stages. The X-ray detector 106 can change the X-ray sensitivity setting in accordance with the processing circuitry 110.

The memory 107 is implemented by, for example, a random access memory (RAM), a semiconductor memory element such as a flash memory, a hard disk, or an optical disk. The memory 107, for example, stores X-ray image data (hereinafter, the X-ray image data is simply referred to as an "X-ray image") generated by the processing circuitry 110. The memory 107 stores time-series history information on the X-ray doses for respective pixel regions of a correction X-ray image based on a second detection result, which will be described later. The pixel region may have, for example, a predetermined size or may be set in the unit of one pixel. The memory 107 stores computer programs corresponding to various functions that the processing circuitry 110 reads and executes.

The display 108 displays various pieces of information. The display 108, for example, displays a GUI for receiving instructions of an operator and various X-ray images under control by the processing circuitry 110. The display 108 is, for example, a liquid crystal display or a CRT display. The display 108 may be a desktop type or may be configured by a tablet terminal capable of making wireless communication with the processing circuitry 110, or the like. The display 108 is also referred to as a display module.

The input interface 109 receives various input operations from the operator, converts the received input operations into electric signals, and outputs them to the processing circuitry 110. The input interface 109 is implemented by, for example, a mouse, a keyboard, a trackball, a switch, a button, a joystick, a touch pad for an input operation by touching an operation surface, a touch screen formed by integrating a display screen and a touch pad, a non-contact input circuitry using an optical sensor, or an audio input circuit. The input interface 109 may be configured by a tablet terminal capable of making wireless communication with the processing circuitry 110, or the like. The input interface 109 is not limited to that including a physical operation component, such as the mouse and the keyboard. Examples of the input interface 109 include electric signal processing circuitry that receives an electric signal corresponding to an input operation from an external input apparatus provided separately from the X-ray diagnostic apparatus 10 and outputs the electric signal to the processing circuitry 110.

The processing circuitry 110 is a processor that reads and executes the computer programs from the memory 107 to implement the functions corresponding to the respective computer programs. The processing circuitry 110 in the embodiment includes a reception function 111, a determination function 112, a first calculation function 113, an imaging control function 114, an acquisition function 115, a generation function 116, a second calculation function 117, a correction function 118, and a display control function 119. The reception function 111 is an example of a receiver. The determination function 112 is an example of a determination module. The first calculation function 113 is an example of a first calculator. The first calculation function 113 is also an example of a calculator. The imaging control function 114 is an example of an imaging controller. The acquisition function 115 is an example of an acquisition module. The generation function 116 is an example of a generator. The second calculation function 117 is an example of a second calculator. The correction function 118 is an example of a corrector. The display control function 119 is an example of a display controller.

The reception function 111, the determination function 112, the first calculation function 113, the imaging control function 114, the acquisition function 115, the generation function 116, the second calculation function 117, the correction function 118, and the display control function 119 as the components of the processing circuitry 110 are stored in the memory 107 in forms of computer-executable programs, for example. The processing circuitry 110 reads the computer programs from the memory 107 and executes the read computer programs to implement the functions corresponding to the computer programs. In other words, the processing circuitry 110 in a state of having read the computer programs has the functions illustrated in the processing circuitry 110 in FIG. 1. In FIG. 1, the single processing circuitry 110 implements the processing functions of the reception function 111, the determination function 112, the first calculation function 113, the imaging control function 114, the acquisition function 115, the generation function 116, the second calculation function 117, the correction function 118, and the display control function 119. Alternatively, the processing functions may be implemented by configuring the processing circuitry 110 by combining a plurality of independent processors and executing the computer programs by the respective processors.

The expression "processor" used in the above explanation means, for example, a central processing unit (CPU), a graphics processing unit (GPU), or a circuit such as an application specific integrated circuit (ASIC) and a programmable logic device (for example, a simple programmable logic device (SPLD), a complex programmable logic device (CPLD), and a field programmable gate array (FPGA)). It should be noted that instead of storage of the computer programs in the memory 107, the computer programs may be directly incorporated in circuitry of the processor. In this case, the processor implements the functions by reading and executing the computer programs incorporated in the circuitry.

The reception function 111 receives various operations by the operator via the input interface 109. The reception function 111 receives, for example, operations by the operator, such as an operation of starting imaging, an operation of specifying the ROI, and input of various imaging conditions. The reception function 111 transmits contents of the received operations to the imaging control function 114 and the first calculation function 113.

The determination function 112 determines exposure conditions of the X-rays and the pulse width of the X-rays by automatic brightness control (ABC) on the basis of the ROI and the various imaging conditions received by the reception function 111. The exposure conditions of the X-rays are, for example, a tube voltage, a tube current, or the like of the X-ray tube. The pulse width that is determined by the ABC is a pulse width for imaging a display X-ray image. The display X-ray image will be described later. Hereinafter, the pulse width for imaging the display X-ray image is referred to as a "specified pulse width". The pulse width of the X-rays may be included in the exposure conditions of the X-rays. The specified pulse width is an example of an exposure period in the embodiment.

The determination function 112 may determine the exposure conditions of the X-rays and the pulse width of the X-rays by automatic exposure control (AEC). The determination function 112 may determine the exposure conditions such that the X-ray tube 102 continuously exposes pulses of the X-rays or may determine the exposure conditions such that the X-ray tube 102 exposes a pulse only once. The determination function 112 transmits the determined exposure conditions to the first calculation function 113 and the imaging control function 114.

The determination function 112 determines the sensitivity setting of the X-ray detector 106 on the basis of the various imaging conditions. The determination function 112 transmits the determined sensitivity setting to the first calculation function 113, the second calculation function 117, and the imaging control function 114.

The first calculation function 113 calculates acquisition timing of the detection results during exposure of the X-rays, that is, the ongoing detection results of the X-rays from the start point of the specified pulse width to an intermediate point of the specified pulse width on the basis of the sensitivity of the X-ray detector 106, the exposure conditions of the X-rays, and the specified pulse width that have been determined by the determination function 112. Hereinafter, the detection result that is acquired in the intermediate point of the specified pulse width is referred to as the second detection result. The acquisition timing of the detection result in the intermediate point of the specified pulse width is referred to as second timing. First timing will be described later.

At the second timing, exposure of the X-rays of the specified pulse width is not completed, and the dose of the X-rays exposed to the detecting elements of the X-ray detector 106 is therefore less than that after the X-rays of the specified pulse width are completely exposed. In the embodiment, the second timing is a fraction of the specified pulse width. The second timing is, for example, one tenth of the specified pulse width and is not however limited thereto. The second timing is, for example, timing at which the X-rays exposed from the X-ray tube 102 are not larger than the maximum incidence dose of the detecting elements of the X-ray detector 106.

For example, there are X-rays, among the X-rays exposed from the X-ray tube 102, that do not pass through the subject P and are directly incident on the detecting elements. When the X-rays of the specified pulse width w are exposed, on the detecting elements receiving direct exposure of the X-rays that do not pass through the subject P, the irradiated X-ray doses are larger than the maximum incidence dose of the detecting elements in some cases. In such a case, in the X-ray image, halation is generated in screen regions corresponding to the detecting elements the irradiated X-ray doses of which are larger than the maximum incident dose of the detecting elements. In this case, detection values (pixel values) are clipped and precise irradiated X-ray doses are unknown for the detecting elements the irradiated X-ray doses of which are larger than a detectable X-ray dose. The second timing is therefore set to timing at which the irradiated X-ray doses are not larger than the maximum incidence dose of the detecting elements of the X-ray detector 106 in order to prevent the halation from being generated in the correction X-ray image.

Since timing at which the halation is generated depends on the sensitivity setting of the X-ray detector 106 and the exposure conditions of the X-rays, the first calculation function 113 adjusts the second timing in accordance with the sensitivity of the X-ray detector 106 and the exposure conditions of the X-rays.

Figure 2:
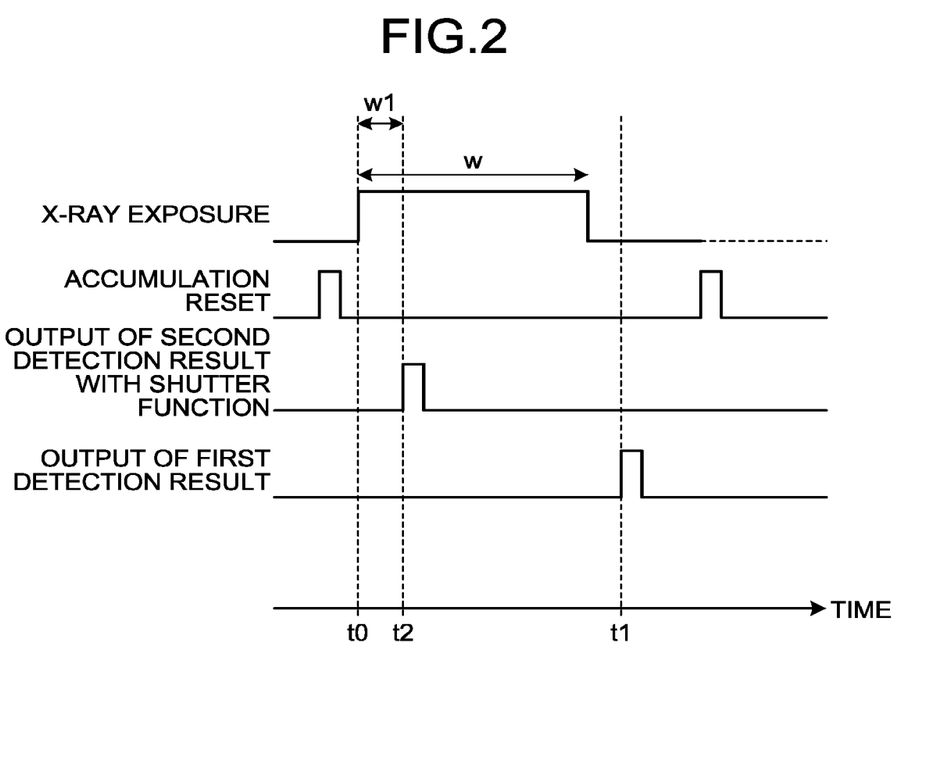
FIG. 2 is a time chart illustrating an example of processing timing in the first embodiment.

FIG. 2 is a time chart illustrating an example of processing timing in the embodiment. A pulse width w illustrated in FIG. 2 indicates the specified pulse width. Timing t0 indicates timing at which the X-ray tube 102 starts exposure of the X-rays. Time t2 illustrated in FIG. 2 is an example of the second timing and is timing at which a time interval w1 shorter than the specified pulse width w has elapsed from the timing t0 at which exposure of the X-rays has been started. The first calculation function 113 transmits the calculated second timing t2 to the imaging control function 114.

With reference back to FIG. 1, the imaging control function 114 controls the X-ray high-voltage generator 101, the X-ray tube 102, the X-ray collimator 103, and the X-ray detector 106 to execute imaging processing of the X-ray image. The imaging control function 114, for example, controls the X-ray high-voltage generator 101, the X-ray tube 102, and the X-ray collimator 103 on the basis of the tube voltage, the tube current, and the like determined as the exposure conditions of the X-rays by the determination function 112, and the specified pulse width w.

The imaging control function 114 controls the X-ray detector 106 to reset electric charges accumulated in the detecting elements of the X-ray detector 106 before an X-ray pulse is exposed.

The imaging control function 114 controls the shutter function of the X-ray detector 106 to output the detection results of the X-rays at the second timing t2 calculated by the first calculation function 113. The detection result of the X-rays at the second timing t2 is referred to as the second detection result. As illustrated in FIG. 2, for example, the imaging control function 114 controls the X-ray detector 106 to output the second detection results at the second timing t2 during exposure of the X-rays of the specified pulse width w.

The imaging control function 114 controls the X-ray detector 106 to output the detection results of the X-rays after the exposure of the X-rays of the specified pulse width w. In the embodiment, timing after the exposure of the X-rays of the specified pulse width w is referred to as the first timing t1. The detection result of the X-rays at the first timing t1 is referred to as the first detection result. In other words, the first detection result is the detection result of the X-rays exposed for the exposure period (specified pulse width w).

The first timing t1 is, for example, timing at which the X-rays are not being exposed after the exposure of the X-rays of the specified pulse width w is completed and before the electric charges accumulated in the X-ray detector 106 are reset, as illustrated in FIG. 2. In the embodiment, the shutter function is not used in the detection at the first timing t1.

With reference back to FIG. 1, the acquisition function 115 acquires, from the X-ray detector 106, the first detection results at the first timing t1 and the second detection results at the second timing t2. Hereinafter, when the first detection results and the second detection results are not particularly distinguished from each other, they are simply referred to as detection results. The acquisition function 115 transmits the acquired detection results to the generation function 116.

The generation function 116 generates the display X-ray image on the basis of the first detection results acquired by the acquisition function 115 and stores the generated display X-ray image in the memory 107. The generation function 116 further generates the correction X-ray image on the basis of the second detection results acquired by the acquisition function 115 and stores the generated correction X-ray image in the memory 107.

The second calculation function 117 calculates the X-ray doses for the respective predetermined pixel regions from the correction X-ray image and stores the calculation results as time-series history information in the memory 107 while correlating the calculation results to the imaging time and the number of imaging times. The history information in the embodiment indicates integrated values of the X-ray doses based on the second detection results.

The predetermined pixel region may include a plurality of pixels or be in the unit of one pixel. As an example, the predetermined pixel region is a region of 2 pixels×2 pixels, which includes two pixels in the lateral direction and two pixels in the longitudinal direction.

Figure 3:
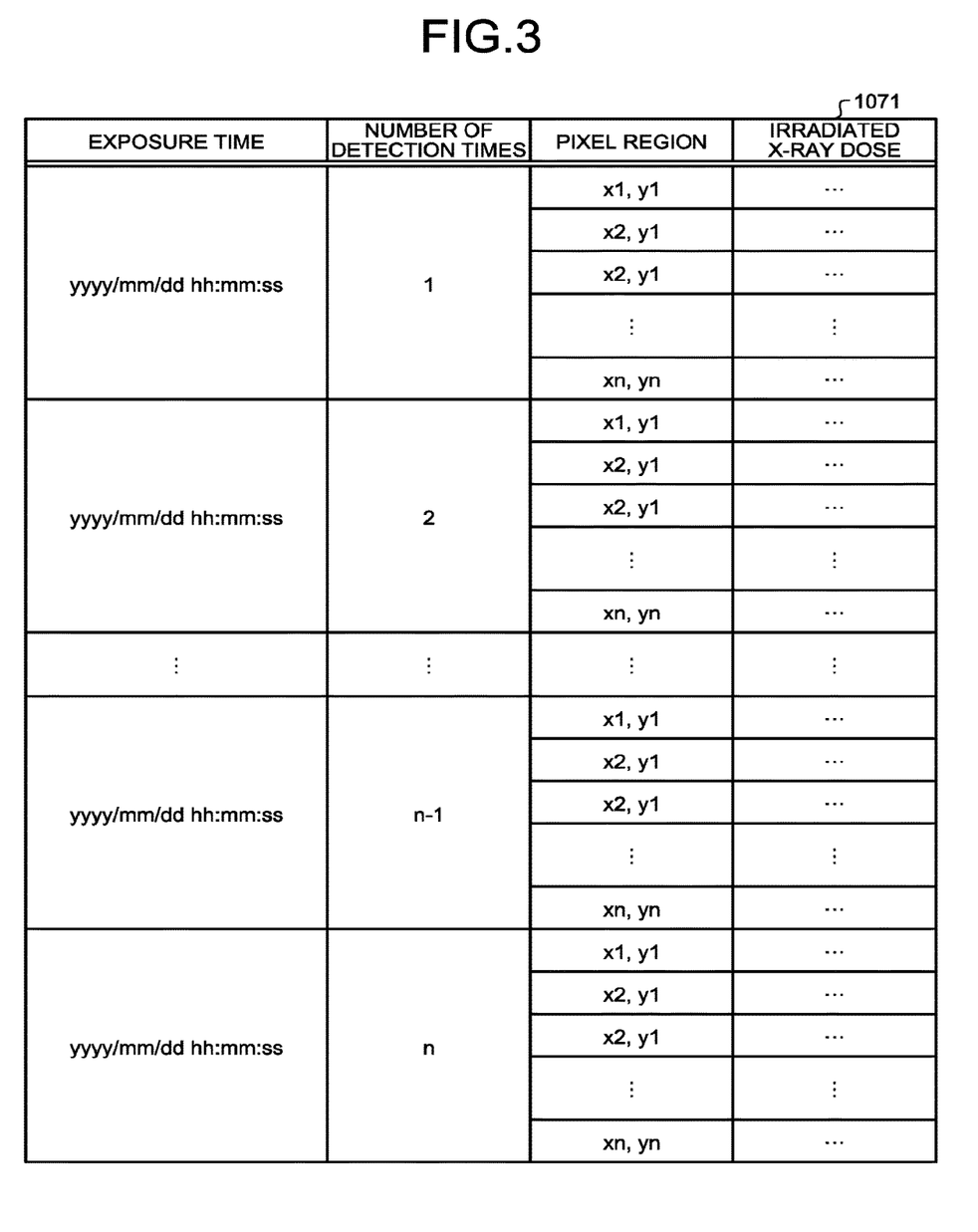
FIG. 3 is a diagram illustrating an example of history information in the first embodiment.

FIG. 3 is a diagram illustrating an example of history information 1071 in the embodiment. As illustrated in FIG. 3, the history information correlates the X-ray exposure time (emission time), the number of detection times, the predetermined pixel region, and the integrated value of the irradiated X-ray doses.

The exposure time is the time when the X-ray detector 106 starts exposure (emission) of the X-rays at each imaging of multiple times. The history information 1071 may include the detection time indicating the second timing t2 in each imaging of multiple times instead of the exposure time. The exposure time (timing t0) is obtained by subtracting the time interval w1 from the detection time. The detection time is also referred to as the imaging time of the correction X-ray image.

The number of detection times is the times for which the second detection results as bases of the correction X-ray image are provided. The number of detection times is also referred to as the number of imaging times of the correction X-ray image.

The integrated value of the irradiated X-ray doses that is registered in the history information 1071 is an integrated value of the irradiated X-ray doses for the number of exposure times in the past when the detecting element(s) corresponding to each predetermined pixel region receive(s) exposure of the X-rays of the specified pulse width w. The irradiated X-ray dose for each exposure is an X-ray dose when the detecting element(s) corresponding to each predetermined pixel region receive(s) the exposure of the X-rays of the specified pulse width w. To be specific, the second calculation function 117 converts the correction X-ray image into an X-ray image for the specified pulse width w and calculates the irradiated X-ray dose for each of the predetermined pixel regions on the basis of the conversion result. The conversion is performed on the basis of a ratio of the specified pulse width w and the time interval w1, and specifically, the second calculation function 117 multiplies the correction X-ray image by a value of "w/w1".

For example, when the second timing t2 is one tenth of the specified pulse width w, the second calculation function 117 multiplies pieces of data of the predetermined pixel regions of the correction X-ray image by 10 to convert the correction X-ray image into the X-ray image when receiving exposure of the X-rays of the specified pulse width w. The second calculation function 117 calculates the irradiated X-ray doses received by the detecting element(s) corresponding to the respective predetermined pixel regions on the basis of the converted X-ray image and the sensitivity setting of the X-ray detector 106 at the exposure time or the detection time.

The second calculation function 117 calculates the irradiated X-ray doses for each imaging of the correction X-ray image and stores, as the history information 1071, the integrated values of the irradiated X-ray doses obtained by adding the calculated irradiated X-ray doses to the past irradiated X-ray doses in the memory 107 while correlating them to the exposure time, the number of detection times, and the predetermined pixel region.

Registration contents of the history information 1071 are deleted when calibration is executed for periodical maintenance or the like. The number of detection times in the history information 1071 is therefore the number of detection times after the previous calibration is executed. That is, first detection of the second detection results after the calibration is executed corresponds to the number of detection times "1".

With reference back to FIG. 1, the correction function 118 corrects the display X-ray image on the basis of the second detection results of the X-rays at the second timing t2. To be more specific, the correction function 118 reads, from the memory 107, the time-series history information 1071 on the X-ray doses for the respective predetermined pixel regions of the correction X-ray image based on the second detection results and corrects the display X-ray image on the basis of the history information 1071.

In the embodiment, artifacts as correction targets are an artifact called "ghosting" and an artifact called "burn-in".

"Ghosting" is the phenomenon in which the sensitivity of the detecting elements included in the X-ray detector 106 is temporarily lowered with the X-rays exposed to the X-ray detector 106 and the contour of a subject (ghost) imaged in the last or more previous imaging appears in the X-ray image. The ghost is moderated or disappears as the sensitivity of the detecting elements recovers with passage of time. Time required for disappearance of the ghost is generally one to two days from exposure of the X-rays but is not limited thereto.

"Burn-in" is the phenomenon in which the sensitivity of the detecting elements included in the X-ray detector 106 becomes non-uniform due to deterioration in the detecting elements with the X-rays exposed to the X-ray detector 106. What the sensitivity of the detecting elements included in the X-ray detector 106 becomes non-uniform is also expressed as generation of sensitivity unevenness in the X-ray detector 106. Burn-in occurs due to the deterioration in the detecting elements and does not therefore recover even when time passes. The degree of lowering of the sensitivity of the detecting elements due to burn-in caused by one exposure of the X-rays is lower than the degree of lowering of the sensitivity of the detecting elements due to ghosting caused by one exposure of the X-rays.

In order to correct the ghost, the correction function 118 calculates a correction coefficient in consideration of recovery of the sensitivity of the X-ray detector 106 with passage of time on the basis of the history information 1071 and corrects the display X-ray image on the basis of the correction coefficient. The recovery of the sensitivity of the X-ray detector 106 with the passage of time is, in other words, attenuation of the ghost with the passage of time.

For example, the correction function 118 inputs the history information 1071 into the following equation (1) to calculate an integrated dose in consideration of the attenuation of the ghost with the passage of time.

$$G(x,y,n)=G(x,y,n-1)e^{-\lambda\Delta t}+R(x,y,n) \quad (1)$$

$G(x, y, n)$ is an integrated dose of the irradiated X-ray dose for each predetermined pixel region in consideration of the attenuation of the ghost after $n^{th}$ detection (that is, after $n^{th}$ X-ray exposure from the previous calibration) by the X-ray detector 106. $G(x, y, n)$ is also considered as an indicator indicating the degree of ghosting for each predetermined pixel region. x and y are coordinates indicating the predetermined pixel region in the X-ray image.

$\lambda$ is a time constant indicating the attenuation of the ghost with the passage of time. $\Delta t$ is a time interval between $(n-1)^{th}$ exposure and $n^{th}$ exposure by the X-ray tube 102. $R(x, y, n)$ is the irradiated X-ray dose in the $n^{th}$ exposure. $R(x, y, n)$ is a result of conversion of the correction X-ray image based on the ratio of the specified pulse width w and the time interval w1 by the above-mentioned second calculation function 117.

That is to say, the integrated dose of the irradiated X-ray dose for each predetermined pixel region in consideration of the attenuation of the ghost after the $n^{th}$ detection by the X-ray detector 106 is a value calculated by adding the irradiated X-ray dose in the $n^{th}$ exposure to the integrated dose of the irradiated X-ray dose for each predetermined pixel region in consideration of the attenuation of the ghost to the $(n-1)^{th}$ exposure.

The correction function 118 calculates a sensitivity correction coefficient $a(x, y, n)$ and an offset correction coefficient $b(x, y, n)$ on the basis of the integrated dose in consideration of the attenuation of the ghost with the passage of time, which has been calculated by the equation (1).

In the embodiment, the correction function 118 corrects the display X-ray image based on the first detection results on the basis of the second detection results with a pulse before a pulse with which the first detection results have been detected. For example, the correction function 118 corrects the display X-ray image based on the first detection results at the first timing after this exposure of the X-rays on the basis of the second detection results at the second timing t2 during the previous exposure of the X-rays. That is to say, the correction function 118 corrects the display X-ray image imaged by this exposure on the basis of the integrated doses to the previous exposure.

When the display X-ray image provided by the $n^{th}$ exposure is corrected, the correction function 118 calculates the sensitivity correction coefficient $a(x, y, n)$ and the offset correction coefficient $b(x, y, n)$ from the integrated dose $G(x, y, n-1)$ in consideration of the attenuation of the ghost to the $(n-1)^{th}$ exposure. For example, values of the integrated dose $G(x, y, n-1)$ in consideration of the attenuation of the ghost, values of the sensitivity correction coefficient $a(x, y, n)$, and values of the offset correction coefficient $b(x, y, n)$ are stored in the memory 107 while being previously correlated with one another. An equation for calculating the values of $a(x, y, n)$ and the values of $b(x, y, n)$ from the values of the integrated dose $G(x, y, n-1)$ in consideration of the attenuation of the ghost may be incorporated in the correction function 118.

The correction function 118 corrects the display X-ray image by using the calculated sensitivity correction coefficient $a(x, y, n)$ and the calculated offset correction coefficient $b(x, y, n)$.

As indicated in the following equation (2), for example, the correction function 118 multiplies a display X-ray image $I_{orig.}(x, y, n)$ imaged by the $n^{th}$ exposure by the sensitivity correction coefficient $a(x, y, n)$ and adds the offset correction coefficient $b(x, y, n)$ thereto to provide a display X-ray image $I_{corr.}(x, y, n)$ after correction.

$$I_{corr.}(x, y, n)=a(x, y, n)I_{orig.}(x, y, n)+b(x, y, n) \quad (2)$$

In the equation (2), the correction function 118 corrects the display X-ray image with the sensitivity correction coefficient $a(x, y, n)$ and the offset correction coefficient $b(x, y, n)$ to compensate for the sensitivity of the detecting elements, which has been lowered due to the incidence of the X-rays, and reduce occurrence of ghosting.

In order to correct burn-in, for example, the correction function 118 calculates the integrated values of the irradiated X-ray doses based on the second detection results on the basis of the history information 1071 and corrects the display X-ray image on the basis of the integrated values.

For example, the correction function 118 inputs the history information 1071 into the following equation (3) to calculate an integrated dose $G'(x, y, n)$ with passage of time. In the equation (3), attenuation with the passage of time is not considered because the burn-in does not attenuate over time.

$$G'(x, y, n)=G'(x, y, n-1)+R(x, y, n) \quad (3)$$

The correction function 118 calculates a sensitivity correction coefficient $a'(x, y, n)$ on the basis of the integrated dose calculated by the equation (3). In the correction of the burn-in, offset correction is not executed. The sensitivity correction coefficient $a'(x, y, n)$ is a value lower than the sensitivity correction coefficient $a(x, y, n)$ that is used for correcting ghosting. The correction function 118 calculates the sensitivity correction coefficient $a'(x, y, n)$ from the integrated dose $G'(x, y, n-1)$ to the $(n-1)^{th}$ exposure. For example, the memory 107 may previously store values of the integrated dose $G'(x, y, n-1)$ and values of the sensitivity correction coefficient a'(x, y, n) in a correlated manner or the correction function 118 may incorporate an equation for calculating the values of the sensitivity correction coefficient a'(x, y, n) from the values of the integrated dose G'(x, y, n−1).

Then, the correction function 118 corrects the display X-ray image by using the calculated sensitivity correction coefficient a'(x, y, n). As indicated in the following equation (4), for example, the correction function 118 multiplies the display X-ray image $I_{orig.}$(x, y, n) imaged by the $n^{th}$ exposure by the sensitivity correction coefficient a'(x, y, n) to provide a display X-ray image $I_{corr.}$(x, y, n) after correction.

$$I_{corr.}(x, y, n) = a'(x, y, n) I_{orig.}(x, y, n) \quad (4)$$

When both the ghost and the burn-in are corrected, the correction function 118 may, for example, input the display X-ray image $I_{corr.}$(x, y, n) after correction, which has been calculated by the equation (2), as the display X-ray image $I_{orig.}$(x, y, n) in the equation (4).

In the embodiment, the correction function 118 corrects the display X-ray image with this exposure on the basis of the integrated dose to the previous exposure. Alternatively, the correction function 118 may correct the display X-ray image with this exposure on the basis of the integrated dose to this exposure. In this case, the correction function 118 calculates the sensitivity correction coefficient a(x, y, n) and the offset correction coefficient b(x, y, n) from the integrated dose G(x, y, n) in consideration of the attenuation of the ghost to the $n^{th}$ exposure. Furthermore, in this case, the correction function 118 calculates the sensitivity correction coefficient a'(x, y, n) from the integrated dose G'(x, y, n) to the nth exposure.

The correction function 118 may execution another processing such as noise correction processing on the display X-ray image. The correction function 118 transmits the display X-ray image after correction to the display control function 119.

The display control function 119 displays the display X-ray image after correction on the display 108.

Next, flow of imaging and correction processing of the X-ray image that the X-ray diagnostic apparatus 10 in the embodiment configured as described above executes.

Figure 4:
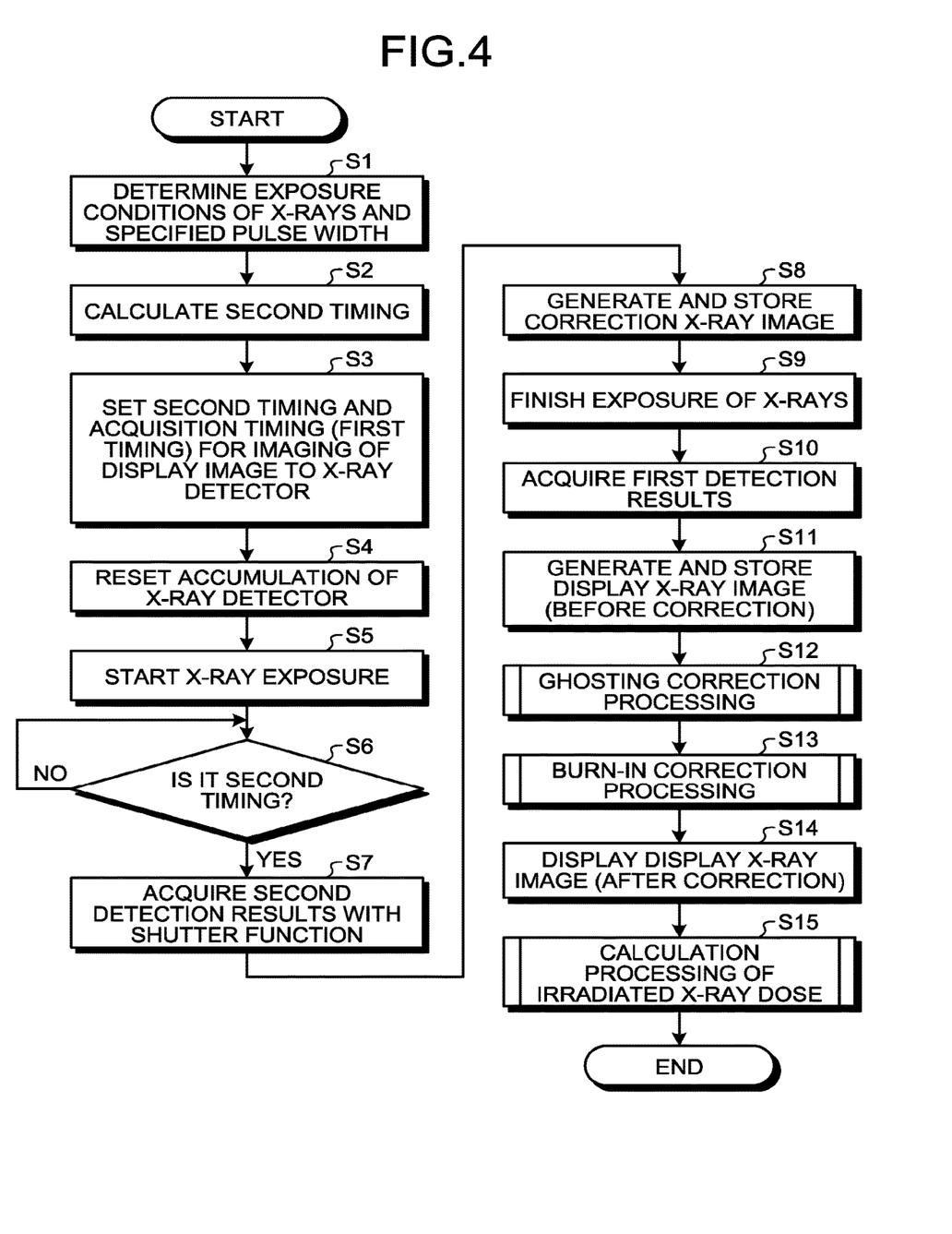
FIG. 4 is a flowchart illustrating an example of flow of imaging and correction processing of an X-ray image in the first embodiment.

FIG. 4 is a flowchart illustrating an example of the flow of the imaging and correction processing of the X-ray image in the embodiment. The processing in the flowchart is started, for example, when the reception function 111 receives an operation of starting imaging by an operator.

First, the determination function 112 determines the exposure conditions of the X-rays, such as the tube voltage and the tube current of the X-ray tube, and the specified pulse width w of the X-rays by the ABC or AEC on the basis of the ROI and various imaging conditions received by the reception function 111 (S1).

Subsequently, the first calculation function 113 calculates acquisition timing (second timing t2) of the detection results during exposure of the X-rays on the basis of the specified pulse width w, the other exposure conditions of the X-rays, and the sensitivity of the X-ray tube 102 (S2).

The imaging control function 114 then sets, in X-ray detector 106, the calculated second timing t2 and acquisition timing (first timing t1) of the detection results for imaging of the display image based on the specified pulse width w (S3).

Thereafter, the imaging control function 114 controls the X-ray detector 106 to reset electric charges accumulated in the detecting elements of the X-ray detector 106 (S4).

The imaging control function 114 then controls the X-ray high-voltage generator 101, the X-ray tube 102, and the X-ray collimator 103 to start exposure (emission) of the X-rays (S5).

The X-ray detector 106 determines whether the current time has reached the second timing t2 set by the imaging control function 114 from the start of the exposure of the X-rays (S6). When the X-ray detector 106 determines that the current time has not reached the second timing t2 (No at S6), it repeats the processing at S6 and stands by.

When the X-ray detector 106 determines that the current time has reached the second timing t2 (Yes at S6), it acquires, as the second detection results, detection results of the X-rays exposed until the second timing t2 with the shutter function (S7). The X-ray detector 106 transmits the second detection results to the processing circuitry 110.

The acquisition function 115 of the processing circuitry 110 acquires the second detection results from the X-ray detector 106. The generation function 116 generates a correction X-ray image on the basis of the second detection results acquired by the acquisition function 115 and stores the generated correction X-ray image in the memory 107 (S8).

The X-ray tube 102 finishes the exposure of the X-rays of the specified pulse width w (S9). The X-ray detector 106 acquires the first detection results at the first timing t1 after the exposure of the X-rays of the specified pulse width w is finished (S10). The X-ray detector 106 transmits the first detection results to the processing circuitry 110.

The acquisition function 115 of the processing circuitry 110 acquires the first detection results from the X-ray detector 106. The generation function 116 generates a display X-ray image on the basis of the first detection results acquired by the acquisition function 115 and stores the generated display X-ray image in the memory 107 (S11). The display X-ray image at this time is the display X-ray image before correction.

Subsequently, the correction function 118 executes the ghosting correction processing on the display X-ray image (S12). Details of the ghosting correction processing will be described later with reference to FIG. 5.

The correction function 118 executes the burn-in correction processing on the display X-ray image after the ghosting correction processing (S13). Details of the burn-in correction processing will be described later with reference to FIG. 6.

Thereafter, the display control function 119 displays the display X-ray image after correction on the display 108 (S14).

The second calculation function 117 then executes calculation processing of the irradiated X-ray dose on the basis of the correction X-ray image generated at S8 (S15). Details of the calculation processing of the irradiated X-ray dose will be described later with reference to FIG. 7. The calculation processing of the irradiated X-ray dose may be executed not after the processing at S14 but in parallel with the pieces of processing at S9 to S14. The irradiated X-ray doses calculated by the second calculation function 117 are stored in the memory 107 as the history information 1071 and are used for the ghosting correction processing and the burn-in correction processing in the next X-ray imaging. The process of this flowchart is ended.

In this flowchart, the imaging control function 114 sets the first timing t1 and the second timing t2 to the X-ray detector 106 before the start of imaging. Alternatively, the imaging control function 114 may instruct the X-ray detector 106 to detect the X-rays at the first timing t1 or the second timing t2.

For example, the imaging control function 114 may determine whether the current time reaches the second timing t2 at S6, and when it determines that the current time reaches the second timing t2, the imaging control function 114 may control the X-ray detector 106 to acquire the second detection results with the shutter function. Furthermore, the imaging control function 114 may control the X-ray detector 106 to acquire the first detection results at the first timing t1 after the exposure of the X-rays of the specified pulse width w is finished at S10.

Figure 5:
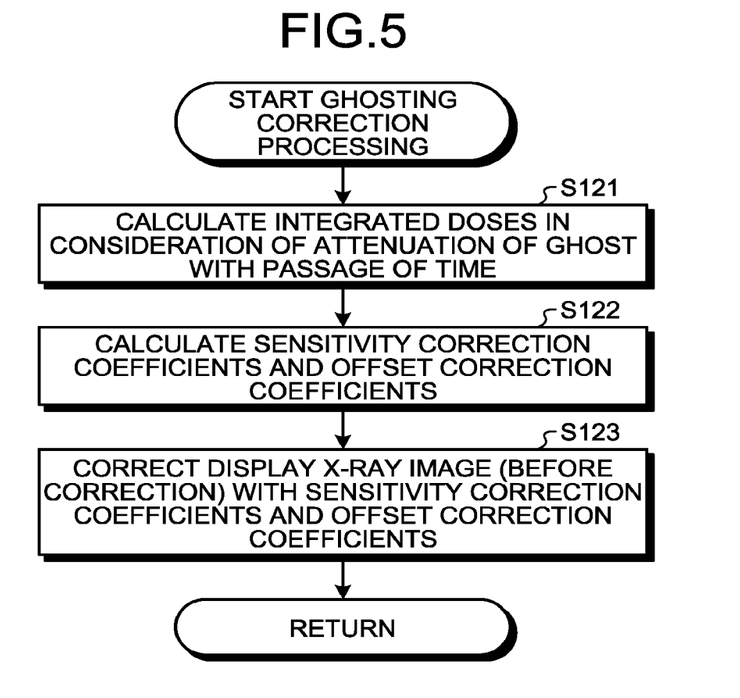
FIG. 5 is a flowchart illustrating an example of flow of ghosting correction processing in the first embodiment.

Next, flow of the ghosting correction processing will be described.

FIG. 5 is a flowchart illustrating an example of the flow of the ghosting correction processing in the embodiment. First, the correction function 118 inputs the history information 1071 into the equation (1) to calculate integrated doses in consideration of attenuation of the ghost with passage of time (S121). The integrated doses in consideration of the attenuation of the ghost with the passage of time, which are calculated here, are integrated doses up to the previous exposure.

For example, when the processing in the flowchart in FIG. 5 is executed after the tenth exposure (this exposure), the irradiated X-ray doses up to the ninth exposure (previous exposure) are stored in the history information 1071. The correction function 118 inputs n=9 into the equation (1) to calculate the integrated doses from the first exposure to the ninth exposure in consideration of the attenuation of the ghost with the passage of time.

Then, the correction function 118 calculates the sensitivity correction coefficients a(x, y, n) and the offset correction coefficients b(x, y, n) on the basis of the integrated doses in consideration of the attenuation of the ghost with the passage of time, which have been calculated by the equation (1) (S122).

The correction function 118 corrects the display X-ray image using a(x, y, n) and the offset correction coefficients b(x, y, n) (S123). With this correction, the artifact with the ghost in the display X-ray image before the correction is reduced. The process of this flowchart is ended and the process returns to the flow in FIG. 4.

Figure 6:
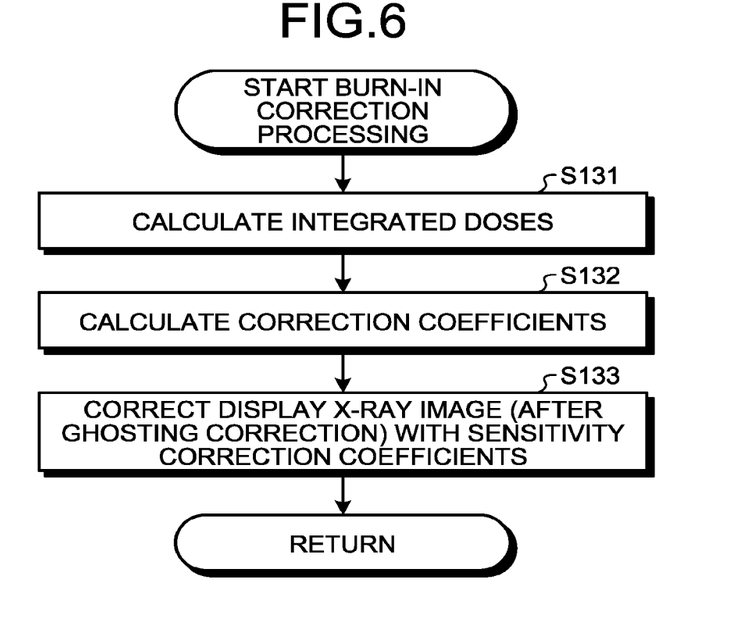
FIG. 6 is a flowchart illustrating an example of flow of burn-in correction processing in the first embodiment.

Next, flow of the burn-in correction processing will be described.

FIG. 6 is a flowchart illustrating an example of the flow of the burn-in correction processing in the embodiment. First, the correction function 118 inputs the history information 1071 into the equation (3) to calculate integrated doses up to the previous exposure (S131).

Then, the correction function 118 calculates the sensitivity correction coefficients a'(x, y, n) on the basis of the integrated doses calculated by the equation (3) (S132).

The correction function 118 corrects, with the sensitivity correction coefficients a'(x, y, n), the display X-ray image after the ghosting correction (S133). With this correction, the artifact with burn-in in the display X-ray image after the ghosting correction is reduced. The process of this flowchart is ended and the process returns to the flow in FIG. 4.

Although the burn-in correction is executed after the ghosting correction in the flowcharts in FIGS. 4 to 6, the order of the ghosting correction and the burn-in correction may be switched. The correction function 118 may execute only one of the ghosting correction and the burn-in correction.

Figure 7:
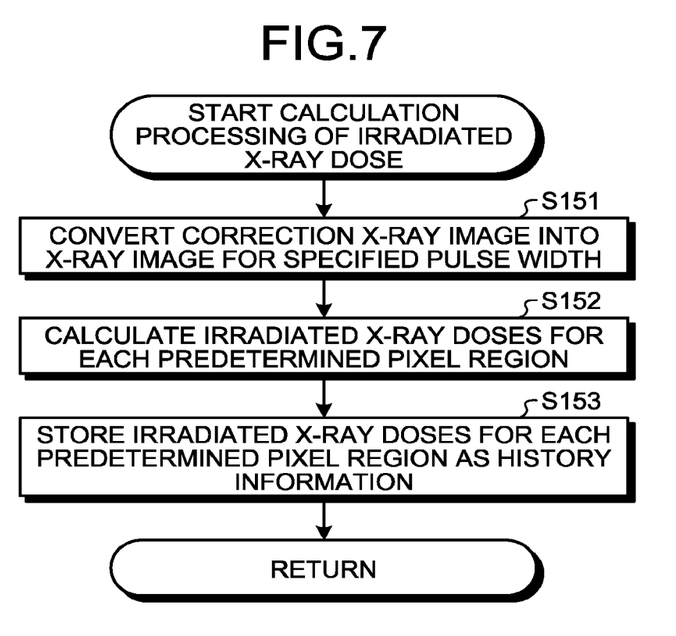
FIG. 7 is a flowchart illustrating an example of calculation processing of an irradiated X-ray dose in the first embodiment.

Next, flow of the calculation processing of the irradiated X-ray dose will be described.

FIG. 7 is a flowchart illustrating an example of the flow of the calculation processing of the irradiated X-ray dose in the embodiment.

First, the second calculation function 117 converts the correction X-ray image into an X-ray image for the specified pulse width w (S151).

Then, the second calculation function 117 calculates the irradiated X-ray doses for the respective predetermined pixel regions on the basis of the X-ray image provided by the conversion in the processing at S151 and the sensitivity setting of the X-ray detector 106 when the correction X-ray image is imaged (that is, the second timing t2) (S152).

The second calculation function 117 stores, in the memory 107, the calculated irradiated X-ray doses for the respective predetermined pixel regions as the history information 1071 (S153). As illustrated in FIG. 3, the second calculation function 117, for example, stores, in the memory 107, the calculated irradiated X-ray doses as the history information 1071 while correlating them to the exposure time, the number of detection times, and the predetermined pixel region. The process of this flowchart is ended and the process returns to the flow in FIG. 4.

In this manner, the X-ray diagnostic apparatus 10 in the embodiment corrects the display X-ray image that is based on the first detection results on the basis of the second detection results, the first detection results being the detection results of the X-rays exposed for the exposure period, the second detection results being the ongoing detection results of the X-rays from the start point of the emission period to an intermediate point of the exposure period. The X-ray diagnostic apparatus 10 in the embodiment can therefore correct the display X-ray image with high accuracy by correcting the display X-ray image using the second detection results in a state in which the total dose of the X-rays to be exposed for the exposure period has not been exposed, that is, in a state in which generation of halation is reduced.

As described above, for example, when the X-rays of the specified pulse width w are exposed, on the detecting elements receiving direct exposure of the X-rays that do not pass through the subject P, the irradiated X-ray doses are larger than the maximum incidence dose of the detecting elements in some cases. In such a case, in the X-ray image, halation is generated in screen regions corresponding to the detecting elements the irradiated X-ray doses of which are larger than the maximum incident dose of the detecting elements. In this case, detection values are clipped and precise irradiated X-ray doses are unknown for the detecting elements the irradiated X-ray doses of which are larger than detectable X-ray dose. In contrast, the X-ray diagnostic apparatus 10 in the embodiment uses, for correction, the second detection results detected at the second timing t2 during the exposure of the X-rays. The detection values are not therefore clipped, and the precise irradiated X-ray doses can be calculated. The phenomena of ghosting and burn-in occur when the sensitivity of the detecting elements is temporarily lowered or irreversibly deteriorated with the X-rays incident on the detecting elements. The X-ray diagnostic apparatus 10 in the embodiment can therefore correct the display X-ray image with high accuracy by correcting the display X-ray image on the basis of the precise irradiated X-ray doses.

The X-ray diagnostic apparatus 10 in the embodiment corrects the display X-ray image on the basis of the time-series history information 1071 on the X-ray doses for the respective pixel regions based on the second detection results stored in the memory 107. The X-ray diagnostic apparatus 10 in the embodiment can therefore correct the display X-ray image with higher accuracy by correcting the display X-ray image in consideration of the temporary lowering of the sensitivity of the detecting elements or deterioration of the detecting elements, which is accumulated by the exposure of multiple times.

The history information 1071 in the embodiment is the integrated values of the X-ray doses based on the second detection results, and the X-ray diagnostic apparatus 10 in the embodiment corrects the display X-ray image on the basis of the integrated values of the X-ray doses. The X-ray diagnostic apparatus 10 in the embodiment can therefore correct the artifacts appearing in the display X-ray image due to progress of the deterioration with increase in the total dose of the X-rays incident on the detecting elements with high accuracy, such as burn-in.

The X-ray diagnostic apparatus 10 in the embodiment calculates the correction coefficients in consideration of recovery of the sensitivity of the X-ray detector 106 with passage of time on the basis of the history information 1071 and corrects the display X-ray image on the basis of the correction coefficients. The X-ray diagnostic apparatus 10 in the embodiment can therefore correct the artifacts appearing in the display X-ray image due to the temporary lowering of the sensitivity of the detecting elements, which is caused by ghosting, with high accuracy by correcting the display X-ray image on the basis of the sensitivity correction coefficients $a(x, y, n)$ and the offset correction coefficients $b(x, y, n)$ in consideration of the recovery of the sensitivity of the X-ray detector 106 with the passage of time, that is, the attenuation of the ghost with the passage of time.

The X-ray diagnostic apparatus 10 in the embodiment corrects the display X-ray image based on the first detection results on the basis of the second detection results with the pulse before the pulse with which the first detection results have been detected. The X-ray diagnostic apparatus 10 in the embodiment can therefore reduce influences, on the display X-ray image as this imaging result, by ghosting, burn-in, or the like accumulated by the X-ray exposure to the previous time.

The X-ray diagnostic apparatus 10 in the embodiment calculates the second timing t2 on the basis of the sensitivity of the X-ray tube 102, the exposure conditions of the X-rays, and the specified pulse width w of the X-rays, and detects the X-rays at the calculated second timing t2. The X-ray diagnostic apparatus 10 in the embodiment can therefore acquire the second detection results that are used for correction at the appropriate second timing t2 each time even when the sensitivity of the X-ray tube 102, the exposure conditions of the X-rays, the specified pulse width w of the X-rays, or the like changes.

Conventionally, a manager or the like executes periodical calibration in order to reduce the ghosting and burn-in correction. On the other hand, the X-ray diagnostic apparatus 10 in the embodiment can correct the ghost and the burn-in with high accuracy, thereby reducing the execution frequency of the periodical calibration. The X-ray diagnostic apparatus 10 in the embodiment can therefore reduce an operation burden on the manager or the like and operation time for the calibration.

In the embodiment, the shutter function is not used in the detection at the first timing t1 for imaging the display X-ray image. The shutter function may however be used in the detection at the first timing t1.

In the embodiment, the first calculation function 113 calculates the second timing t2 on the basis of the sensitivity of the X-ray tube 102, the exposure conditions of the X-rays, and the specified pulse width w of the X-rays. The calculation method of the second timing t2 is not however limited thereto. For example, a ratio of the second timing t2 in the specified pulse width w may be previously set to "one tenth" or the like. In this case, the first calculation function 113 calculates the second timing t2 on the basis of the specified pulse width w and the previously set ratio.

When the X-ray tube 102 continuously exposes pulses of the X-rays, the first calculation function 113 may change the second timing t2 in a subsequent pulse on the basis of the display X-ray image or the correction X-ray image that has been imaged. For example, the first calculation function 113 may extend the time interval w1 to the second timing t2 from timing t0 at which exposure of the X-rays in $(n+1)^{th}$ exposure of the X-rays is started when it is determined, on the basis of the display X-ray image or the correction X-ray image imaged by the nth exposure of the X-rays, that halation is not generated even after the present second timing t2.

Second Embodiment

In the first embodiment, the X-ray diagnostic apparatus 10 executes the ghosting correction and the burn-in correction on the display X-ray image. In a second embodiment, scattered-ray correction is further executed.

A grid for reducing the dose of scattered rays incident on the detecting elements is provided on the surface of the X-ray detector 106. There are however the scattered rays incident on the detecting elements without being removed by the grid. The scattered rays incident on the detecting elements become noise in the display X-ray image and cause lowering of a contrast of the display X-ray image. Image processing for reducing influences on the display X-ray image by the scattered rays is referred to as the scattered-ray correction.

Hereinafter, the X-ray diagnostic apparatus 10 in the embodiment will be described.

As in the first embodiment, the X-ray diagnostic apparatus 10 in the embodiment includes the X-ray high-voltage generator 101, the X-ray tube 102, the X-ray collimator 103, the tabletop 104, the C arm 105, the X-ray detector 106, the memory 107, the display 108, the input interface 109, and the processing circuitry 110.

The processing circuitry 110 includes the reception function 111, the determination function 112, the first calculation function 113, the imaging control function 114, the acquisition function 115, the generation function 116, the second calculation function 117, the correction function 118, and the display control function 119.

The reception function 111, the determination function 112, the first calculation function 113, the imaging control function 114, the acquisition function 115, the generation function 116, the second calculation function 117, and the display control function 119 have the same functions as those in the first embodiment.

The correction function 118 in the embodiment has the function in the first embodiment and further performs the scattered-ray correction on the display X-ray image based on the first detection results on the basis of the second detection results based on the same pulse as that of the first detection results. That is to say, the correction function 118 corrects the display X-ray image read after exposure of the pulse is completed using a correction X-ray image read in the intermediate point of the exposure of the pulse.

To be more specific, for example, the scattering correction is executed on the basis of an equation (5). To be specific, the correction function 118 computes convolutional integration of the correction X-ray image and a scattered-ray function S to calculate a scattered-ray component. The correction function 118 subtracts the calculated scattered-ray component from the display X-ray image to reduce influences of the scattered rays on the display X-ray image.

$$I_{corr.}(x, y, n) = I_{orig.}(x, y, n) - R(x, y, n) * s \quad (5)$$

Figure 8:
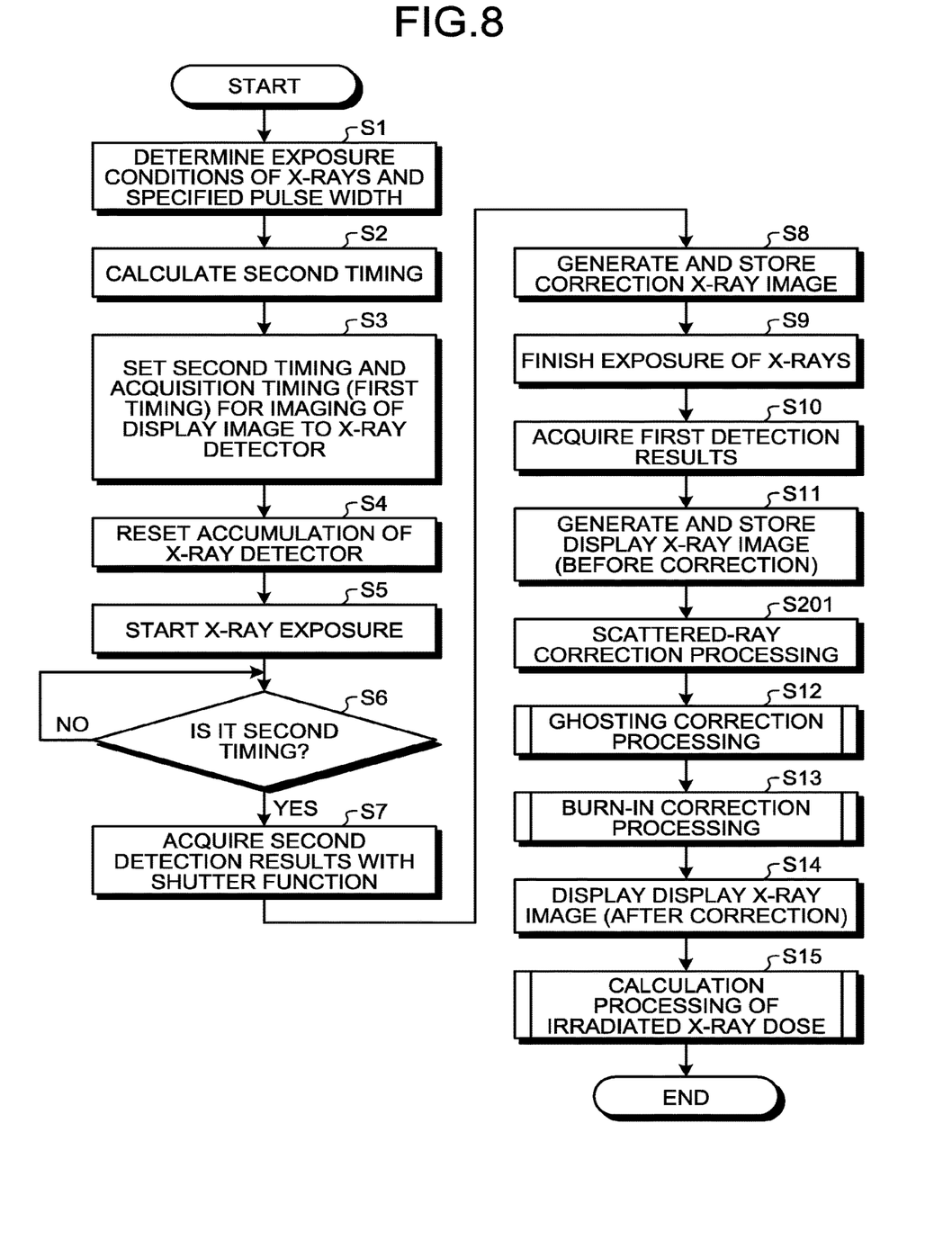
FIG. 8 is a flowchart illustrating an example of flow of imaging and correction processing of an X-ray image according to a second embodiment.

FIG. 8 is a flowchart illustrating an example of flow of imaging and correction processing of the X-ray image in the embodiment. The processing of determining the exposure conditions and the specified pulse width of the X-rays at S1 to the processing of generating and storing the display X-ray image (before correction) at S11 are the same as those in the first embodiment.

Then, the correction function 118 in the embodiment executes the scattered-ray correction processing on the display X-ray image on the basis of the correction X-ray image generated by the processing at S8 (S201). In the ghosting correction processing at S12, the ghosting correction is executed on the display X-ray image after the scattered-ray correction processing. The burn-in correction processing at S13 to the calculation processing of the irradiated X-ray dose at S15 are the same as those in the first embodiment.

Thus, the X-ray diagnostic apparatus 10 in the embodiment corrects the display X-ray image based on the first detection results at the last first timing on the basis of the second detection results at the last second timing t2 to thereby reduce influences on the display X-ray image by scattered rays generated during imaging of the display X-ray image with high accuracy.

As a comparative example, for example, there is a technique of performing scattered-ray correction on a display X-ray image (raw image) as a correction target by estimating a scattered-ray component in the display X-ray image by convolution of a scattered-ray function and subtracting the estimated scattered-ray component from the display X-ray image. In such a technique, the scattered-ray component is directly estimated from the display X-ray image. It can therefore be difficult to estimate the scattered-ray component with high accuracy when there is a region in which detection values (pixel values) are clipped due to generation of halation or the like in the display X-ray image.

Another comparative example is a technique of performing scattered-ray correction in a spatial frequency region using Fourier transformation. Also in this technique, it can be difficult to estimate a scattered-ray component with high accuracy when there is a region in which detection values (pixel values) are clipped in the display X-ray image as a base of calculation of the scattered-ray component.

In contrast, the X-ray diagnostic apparatus 10 in the embodiment can execute the scattered-ray correction on the basis of the precise irradiated X-ray doses by correcting the display X-ray image using the second detection results in a state in which the total dose of the X-rays of the specified pulse width w has not been exposed, that is, in a state in which generation of halation is reduced.

Although in the embodiment, the X-ray diagnostic apparatus 10 executes the ghosting correction, the burn-in correction, and the scattered-ray correction, only the scattered-ray correction may be executed.

Third Embodiment

In the first and second embodiments, the X-ray diagnostic apparatus 10 executes various pieces of processing. Embodiments are not however limited thereto, and a medical image processing apparatus provided separately from the X-ray diagnostic apparatus 10 may execute the above-mentioned pieces of processing.

Figure 9:
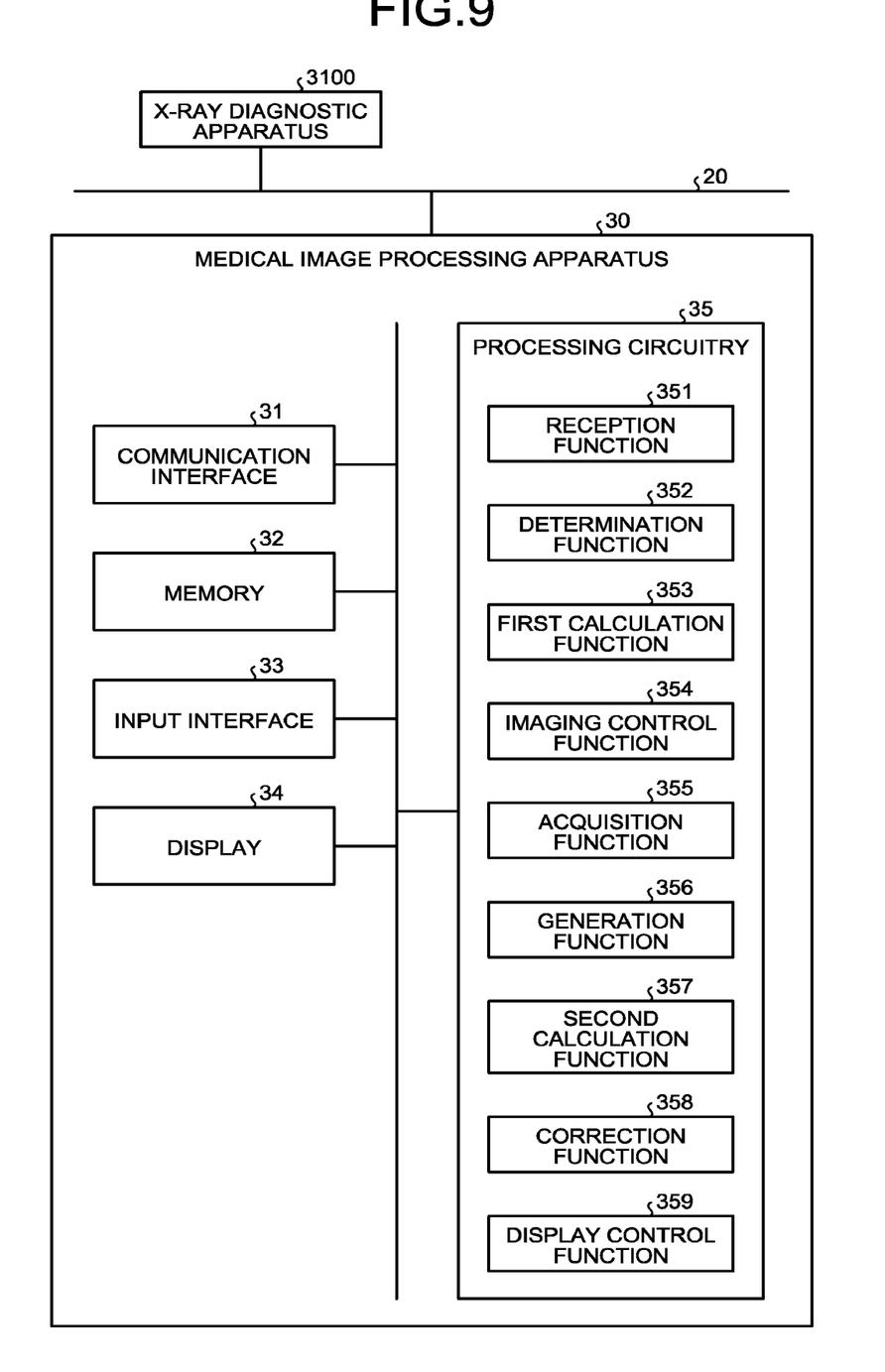
FIG. 9 is a diagram illustrating an example of the configuration of a medical image processing apparatus according to a third embodiment.

FIG. 9 is a diagram illustrating an example of the configuration of a medical image processing apparatus 30 according to the embodiment. The medical image processing apparatus 30 is a server apparatus, a personal computer (PC), or the like installed in a hospital, for example. As illustrated in FIG. 9, the medical image processing apparatus 30 includes a communication interface 31, a memory 32, an input interface 33, a display 34, and processing circuitry 35.

The communication interface 31 is connected to the processing circuitry 35 and controls transfer of various pieces of data to/from and communication with the X-ray diagnostic apparatus 3100 connected thereto via a network 20. The communication interface 31 is implemented by, for example, a network card, a network adapter, or a network interface controller (NIC). In the embodiment, the communication interface 31 receives the first detection results and the second detection results from the X-ray diagnostic apparatus 3100 and outputs the received first detection results and the received second detection results to the processing circuitry 35.

The memory 32 has the same function as that of the memory 107 described in the first embodiment. The input interface 33 has the same function as that of the input interface 109 described in the first embodiment. The display 34 has the same function as that of the display 108 described in the first embodiment.

The processing circuitry 35 is a processor that reads and executes computer programs from the memory 32 to implement functions corresponding to the computer programs. The processing circuitry 35 has a reception function 351, a determination function 352, a first calculation function 353, an imaging control function 354, an acquisition function 355, a generation function 356, a second calculation function 357, a correction function 358, and a display control function 359. The processing circuitry 35 has the same functions as those of the processing circuitry 110 described in the first embodiment. The processing circuitry 35 may have the same function as any of the functions of the processing circuitry 110 described in the second embodiment. In the embodiment, the processing circuitry 35 may display the display X-ray image after correction on the display 34 of the medical image processing apparatus 30 or transmit it to the X-ray diagnostic apparatus 3100.

Modifications

Although the X-ray detector 106 has the CMOS sensors as the detecting elements in each of the above-mentioned embodiments, the detecting elements are not limited thereto. The X-ray detector 106 may have charge coupled device (CCD) sensors, for example.

In the case in which the CCD sensors are used, when the detection results are read at the second timing t2 before the end of the exposure of the X-rays of the specified pulse width w, electric charges accumulated from the start of the exposure of the X-rays to the second timing t2 are output and the accumulation is reset. In the modification, the generation function 116 of the processing circuitry 110 therefore sums up a correction X-ray image based on the second detection results detected at the second timing t2 and an X-ray image based on the first detection results detected at the first timing t1 to generate a display X-ray image.

At least one of the embodiments described above can correct an X-ray image with high accuracy.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic apparatus comprising:
    an X-ray tube configured to expose X-rays;
    an X-ray detector configured to detect the X-rays exposed by the X-ray tube; and
    processing circuitry configured to
        generate an X-ray image by using a first detection result that is a detection result of the X-rays exposed for an exposure period, and
        correct the X-ray image by using a second detection result that is a detection result of the X-rays until a point before an end of the exposure period.

2. The X-ray diagnostic apparatus according to claim 1, further comprising a memory configured to store time-series history information on X-ray dose for each pixel region based on the second detection result, wherein
    the processing circuitry corrects the X-ray image by using the history information.

3. The X-ray diagnostic apparatus according to claim 2, wherein
    the history information is an integrated value of X-ray doses based on the second detection results, and
    the processing circuitry corrects the X-ray image by using the integrated value.

4. The X-ray diagnostic apparatus according to claim 2, wherein
    the processing circuitry is configured to
        calculate a correction coefficient in consideration of recovery of sensitivity of the X-ray detector with passage of time by using the history information, and
        correct the X-ray image by using the correction coefficient.

5. The X-ray diagnostic apparatus according to claim 1, wherein
    the X-ray tube exposes the X-rays of a specified pulse width multiple times, and
    the processing circuitry corrects the X-ray image based on the first detection result by using the second detection result with a pulse before a pulse with which the first detection result has been detected.

6. The X-ray diagnostic apparatus according to claim 1, wherein
    the X-ray tube exposes the X-rays of a specified pulse width multiple times, and
    the processing circuitry corrects the X-ray image based on the first detection result by using the second detection result with a pulse same as a pulse of the first detection result.

7. The X-ray diagnostic apparatus according to claim 1, wherein
    the processing circuitry calculates acquisition timing of the second detection result by using sensitivity of the X-ray detector, exposure conditions of the X-rays, and a specified pulse width of the X-rays, and
    the X-ray detector detects the X-rays exposed until the calculated acquisition timing with a shutter function.

8. A medical image processing apparatus comprising processing circuitry configured to
    generate an X-ray image by using a first detection result that is a detection result of X-rays exposed for an exposure period, and
    correct the X-ray image by using a second detection result that is a detection result of the X-rays until a point before an end of the exposure period.

9. A medical image processing method comprising:
    generating an X-ray image by using a first detection result that is a detection result of X-rays exposed for an exposure period, and
    correcting the X-ray image by using a second detection result that is a detection result of the X-rays until a point before an end of the exposure period.

10. The medical image processing method according to claim 9, wherein at the correcting, the X-ray image is corrected by using time-series history information on X-ray dose for each pixel region based on the second detection result.

11. The medical image processing method according to claim 10, wherein
    the history information is an integrated value of X-ray doses based on the second detection results, and
    at the correcting, the X-ray image is corrected by using the integrated value.

12. The medical image processing method according to claim 10, wherein
    at the correcting, a correction coefficient is calculated in consideration of recovery of sensitivity with passage of time of an X-ray detector configured to detect the X-rays by using the history information, and
    the X-ray image is corrected by using the correction coefficient.

13. The medical image processing method according to claim 9, wherein
    the X-rays of a specified pulse width are exposed multiple times, and
    at the correcting, the X-ray image based on the first detection result is corrected by using the second detection result with a pulse before a pulse with which the first detection result has been detected.

14. The medical image processing method according to claim 9, wherein
    the X-rays of a specified pulse width are exposed multiple times, and
    at the correcting, the X-ray image based on the first detection result is corrected by using the second detection result with a pulse same as a pulse of the first detection result.

15. The medical image processing method according to claim 9, further comprising calculating acquisition timing of the second detection result by using sensitivity of an X-ray detector configured to detect the X-rays, exposure conditions of the X-rays, and a specified pulse width of the X-rays.

* * * * *